(12) United States Patent
Bienvenu

(10) Patent No.: US 8,333,801 B2
(45) Date of Patent: Dec. 18, 2012

(54) METHOD OF FORMING A DRUG-ELUTING MEDICAL DEVICE

(75) Inventor: Ryan Bienvenu, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 308 days.

(21) Appl. No.: 12/884,343

(22) Filed: Sep. 17, 2010

(65) Prior Publication Data

US 2012/0067008 A1   Mar. 22, 2012

(51) Int. Cl.
*A61F 2/06* (2006.01)
*A61F 2/82* (2006.01)
*A61F 2/90* (2006.01)
*B23P 15/00* (2006.01)

(52) U.S. Cl. ............... 623/1.42; 623/1.15; 623/1.22; 623/1.23; 623/1.27; 623/1.39; 29/458; 29/557; 216/56; 216/75; 216/83; 216/96; 216/100

(58) Field of Classification Search .......... 29/458, 29/557; 623/1.15, 1.22, 1.23, 1.27, 1.39, 623/1.42; 216/56, 75, 83, 96, 100
See application file for complete search history.

(56) References Cited

U.S. PATENT DOCUMENTS

| | | | |
|---|---|---|---|
| 2,153,936 A | 4/1939 | Owens et al. |
| 4,531,933 A | 7/1985 | Norton et al. |
| 4,643,716 A | 2/1987 | Drach |
| 4,720,384 A | 1/1988 | DiLuccio et al. |
| 4,763,647 A | 8/1988 | Gambale |
| 4,800,082 A | 1/1989 | Karbowski et al. |
| 4,800,882 A | 1/1989 | Gianturco |
| 4,813,925 A | 3/1989 | Anderson, Jr. |
| 4,886,062 A | 12/1989 | Wiktor |
| 4,913,683 A | 4/1990 | Gregory |
| 5,019,090 A | 5/1991 | Pinchuk |
| 5,063,935 A | 11/1991 | Gambale |
| 5,133,732 A | 7/1992 | Wiktor |
| 5,154,705 A | 10/1992 | Fleishhacker et al. |
| 5,234,456 A | 8/1993 | Silvestrini |
| 5,306,250 A | 4/1994 | March et al. |

(Continued)

FOREIGN PATENT DOCUMENTS

EP   836839 A2   10/1997

(Continued)

OTHER PUBLICATIONS

U.S. Appl. No. 12/428,581, filed Apr. 23, 2009, Hoff et al.

(Continued)

*Primary Examiner* — Derris Banks
*Assistant Examiner* — Anthony Green

(57) ABSTRACT

A method of forming a stent includes the steps of forming an elongated composite member or plurality of elongated composite members into a stent pattern having struts interconnected by crowns, the composite member including an outer member and a core member. Openings are formed through the outer member of the composite member. The composite member is processed to remove the core member from at least a plurality of the struts of the stent without adversely affecting the outer member and such that the core member is not removed from at least a plurality of the crowns of the stent, thereby leaving the outer member with a lumen in at least a plurality of the struts and the outer member with the core member in at least a plurality of the crowns. The lumens may then be filled with a biologically or pharmacologically active substance.

24 Claims, 14 Drawing Sheets

U.S. PATENT DOCUMENTS

| | | | |
|---|---|---|---|
| 5,345,945 A | 9/1994 | Hodgson et al. | |
| 5,536,274 A | 7/1996 | Neuss | |
| 5,538,735 A | 7/1996 | Ahn | |
| 5,569,197 A | 10/1996 | Helmus et al. | |
| 5,605,162 A | 2/1997 | Mirzaee et al. | |
| 5,630,840 A | 5/1997 | Mayer | |
| 5,670,161 A | 9/1997 | Healy et al. | |
| 5,782,903 A | 7/1998 | Wiktor | |
| 5,795,318 A | 8/1998 | Wang et al. | |
| 5,824,045 A | 10/1998 | Alt | |
| 5,843,117 A | 12/1998 | Alt et al. | |
| 5,882,335 A | 3/1999 | Leone et al. | |
| 5,891,108 A | 4/1999 | Leone et al. | |
| 5,902,266 A | 5/1999 | Leone et al. | |
| 5,957,903 A | 9/1999 | Mirzaee et al. | |
| 6,022,369 A | 2/2000 | Jacobsen et al. | |
| 6,063,101 A | 5/2000 | Jacobsen et al. | |
| 6,071,305 A | 6/2000 | Brown et al. | |
| 6,099,561 A | 8/2000 | Alt | |
| 6,136,023 A | 10/2000 | Boyle | |
| 6,248,190 B1 | 6/2001 | Stinson | |
| 6,358,276 B1 | 3/2002 | Edwin | |
| 6,364,902 B1 | 4/2002 | Dickenson et al. | |
| 6,478,778 B1 | 11/2002 | Jacobsen et al. | |
| 6,497,709 B1 | 12/2002 | Heath | |
| 6,558,422 B1 | 5/2003 | Baker et al. | |
| 6,623,519 B2 | 9/2003 | Edwin | |
| 6,641,607 B1 | 11/2003 | Hossainy et al. | |
| 6,656,162 B2 | 12/2003 | Santini, Jr. et al. | |
| 6,699,281 B2 | 3/2004 | Vallana et al. | |
| 6,752,829 B2 | 6/2004 | Kocur et al. | |
| 6,764,505 B1* | 7/2004 | Hossainy et al. | 623/1.15 |
| 6,783,543 B2 | 8/2004 | Jang | |
| 6,989,071 B2 | 1/2006 | Kocur et al. | |
| 7,041,130 B2 | 5/2006 | Santini, Jr. et al. | |
| 7,044,965 B1 | 5/2006 | Spielberg | |
| 7,060,093 B2 | 6/2006 | Dang et al. | |
| 7,101,392 B2 | 9/2006 | Heath | |
| 7,104,130 B2* | 9/2006 | Kenny et al. | 73/514.33 |
| 7,122,048 B2 | 10/2006 | Dimatteo et al. | |
| 7,135,039 B2 | 11/2006 | De Scheerder et al. | |
| 7,288,084 B2 | 10/2007 | Li | |
| 7,344,563 B2 | 3/2008 | Vallana et al. | |
| 7,384,660 B2 | 6/2008 | Hossainy et al. | |
| 7,575,593 B2* | 8/2009 | Rea et al. | 623/1.42 |
| 2002/0065548 A1 | 5/2002 | Birdsall et al. | |
| 2002/0087209 A1 | 7/2002 | Edwin et al. | |
| 2002/0103527 A1 | 8/2002 | Kocur et al. | |
| 2002/0138048 A1 | 9/2002 | Tuch | |
| 2003/0021825 A1 | 1/2003 | Pathak et al. | |
| 2003/0068353 A1 | 4/2003 | Chen et al. | |
| 2003/0125803 A1 | 7/2003 | Vallana et al. | |
| 2003/0208256 A1 | 11/2003 | DiMatteo et al. | |
| 2004/0006382 A1 | 1/2004 | Sohier | |
| 2004/0023339 A1 | 2/2004 | Boyle | |
| 2004/0024449 A1 | 2/2004 | Boyle | |
| 2004/0037889 A1 | 2/2004 | Richeal et al. | |
| 2004/0106984 A1 | 6/2004 | Stinson | |
| 2004/0133270 A1 | 7/2004 | Grandt | |
| 2004/0148012 A9 | 7/2004 | Jang | |
| 2005/0043783 A1 | 2/2005 | Amis et al. | |
| 2005/0055080 A1 | 3/2005 | Istephanous et al. | |
| 2005/0060020 A1 | 3/2005 | Jenson | |
| 2005/0060861 A1 | 3/2005 | Bradley | |
| 2005/0070996 A1 | 3/2005 | Dinh et al. | |
| 2005/0080481 A1 | 4/2005 | Madda et al. | |
| 2005/0145307 A1 | 7/2005 | Shireman et al. | |
| 2005/0177226 A1 | 8/2005 | Banik et al. | |
| 2005/0186241 A1 | 8/2005 | Boyle et al. | |
| 2005/0208100 A1 | 9/2005 | Weber et al. | |
| 2005/0272806 A1 | 12/2005 | Falotico et al. | |
| 2005/0278016 A1 | 12/2005 | Welsh et al. | |
| 2006/0004437 A1 | 1/2006 | Jayaraman | |
| 2006/0064157 A1 | 3/2006 | Shanley | |
| 2006/0122689 A1 | 6/2006 | Kocur et al. | |
| 2006/0129231 A1* | 6/2006 | De Scheerder et al. | 623/1.16 |
| 2006/0147489 A1 | 7/2006 | Shanley et al. | |
| 2006/0155369 A1 | 7/2006 | Edwin et al. | |
| 2006/0212109 A1 | 9/2006 | Sirhan et al. | |
| 2006/0224234 A1 | 10/2006 | Jayaraman | |
| 2006/0224237 A1 | 10/2006 | Furst et al. | |
| 2007/0005124 A1 | 1/2007 | De Scheerder et al. | |
| 2007/0027531 A1* | 2/2007 | DiMatteo et al. | 623/1.42 |
| 2007/0043423 A1 | 2/2007 | Grewe | |
| 2007/0055352 A1 | 3/2007 | Naimark et al. | |
| 2007/0061007 A1 | 3/2007 | Nolting | |
| 2007/0112417 A1 | 5/2007 | Shanley et al. | |
| 2007/0123805 A1 | 5/2007 | Shireman et al. | |
| 2007/0168021 A1 | 7/2007 | Holmes, Jr. et al. | |
| 2007/0173923 A1 | 7/2007 | Savage et al. | |
| 2007/0219628 A1 | 9/2007 | Shanley et al. | |
| 2007/0282419 A1 | 12/2007 | Hilaire et al. | |
| 2008/0003251 A1 | 1/2008 | Zhou | |
| 2008/0051882 A1 | 2/2008 | Rubin | |
| 2008/0065201 A1 | 3/2008 | Li | |
| 2008/0077233 A1 | 3/2008 | Diaz et al. | |
| 2008/0183281 A1 | 7/2008 | Rea et al. | |
| 2008/0188925 A1 | 8/2008 | Zhao | |
| 2008/0195170 A1 | 8/2008 | Asgari | |
| 2008/0195196 A1 | 8/2008 | Asgari | |
| 2008/0234809 A1 | 9/2008 | Greenan | |
| 2008/0249599 A1 | 10/2008 | Allen et al. | |
| 2008/0255659 A1 | 10/2008 | Huang et al. | |
| 2008/0276935 A1 | 11/2008 | Wang | |
| 2008/0306579 A1 | 12/2008 | Dolan et al. | |
| 2009/0024209 A1 | 1/2009 | Ozdil et al. | |
| 2009/0024210 A1* | 1/2009 | Klocke et al. | 623/1.42 |
| 2009/0035351 A1 | 2/2009 | Berglund et al. | |
| 2009/0061071 A1 | 3/2009 | McMorrow et al. | |
| 2009/0093871 A1 | 4/2009 | Rea et al. | |
| 2009/0132031 A1 | 5/2009 | Cook et al. | |
| 2009/0157172 A1 | 6/2009 | Kokate et al. | |
| 2009/0163995 A1 | 6/2009 | Shanley et al. | |
| 2009/0192593 A1* | 7/2009 | Meyer et al. | 623/1.42 |
| 2009/0220612 A1 | 9/2009 | Perera | |
| 2009/0228095 A1 | 9/2009 | Shanley et al. | |
| 2009/0281615 A1 | 11/2009 | Kocur et al. | |
| 2009/0312833 A1 | 12/2009 | Tittelbach et al. | |
| 2009/0319026 A1 | 12/2009 | Meyer | |
| 2010/0010621 A1 | 1/2010 | Klocke | |
| 2010/0023115 A1* | 1/2010 | Robaina et al. | 623/1.42 |
| 2010/0036482 A1 | 2/2010 | Svrluga et al. | |
| 2010/0057196 A1 | 3/2010 | Pathak | |
| 2010/0070022 A1* | 3/2010 | Kuehling | 623/1.16 |
| 2010/0082096 A1 | 4/2010 | Gregorich | |
| 2010/0145437 A1* | 6/2010 | Girton et al. | 623/1.42 |

FOREIGN PATENT DOCUMENTS

| | | |
|---|---|---|
| EP | 080998 A2 | 12/1997 |
| EP | 1600534 | 11/2005 |
| EP | 836839 B1 | 7/2006 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO02/060506 | 8/2002 |
| WO | WO03/092547 | 11/2003 |
| WO | WO2007/021749 | 2/2007 |
| WO | 2009/064618 A1 | 5/2009 |

OTHER PUBLICATIONS

U.S. Appl. No. 12/500,359, filed Jul. 9, 2009, Storment et al.

Derle et al., "Particle Engineering Techniques to Enhance Dissolution of Poorly Water Soluble Drugs" International Journal of Current Pharmaceutical Research, vol. 2, Issue 1, 2010, pp. 10-15.

Purvis et al., "Cryogenic Liquids, Nanoparticles, and Microencapsulation" International Journal of Pharmaceutics, 2006.

"Supercritical Carbon-Dioxide Cleaning Defined" Supercritical Carbon-Dioxide Cleaning Technology Review, Jul. 1996.

Berger "Coating Drug-Eluting Arterial Stents Using Ultrasonic Spray Nozzle" ILASS Americas, 19$^{th}$ Annual Conference on Liquid Atomization and Spray Systems, May 2006.

U.S. Appl. No. 09/716,146, filed Nov. 17, 2000, Boyle.

Basarir et al., "Osseointegration in Arthroplasty: Can Simvastatin Promote one response to Implants?"International Orthopedics (SICOT) (2009) 33:855-859.

Polacco et al. "Biodegradable Hollow Fibres Containing Drug-Loaded Nanoparticles as Controlled Release Systems" Polym International 51:1464-1472 (2002).

PCT Search Report PCT/US2010/039087.
PCT Search Report PCT/US2010/049439.
PCT Search Report PCT/US2010/049437.
PCT Search Report PCT/US2010/049434.

* cited by examiner

METHOD OF FORMING A DRUG-ELUTING MEDICAL DEVICE

FIELD OF THE INVENTION

The present invention relates to implantable medical devices that release biologically or pharmacologically active substances and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer biologically or pharmacologically active substances such as anti-inflammatory compounds that block local invasion/activation of monocytes, thus preventing the secretion of growth factors that may trigger VSMC proliferation and migration. Other potentially anti-restenotic compounds include anti-proliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a biologically or pharmacologically active substance or a combination of biologically or pharmacologically active substances. Once the medical device is implanted at a target location, the biologically or pharmacologically active substance is released from the polymer for treatment of the local tissues. The biologically or pharmacologically active substance is released by a process of diffusion through the polymer layer for biostable polymers, and/or as the polymer material degrades for biodegradable polymers.

Controlling the rate of elution of a biologically or pharmacologically active substance from the impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug-impregnated polymer coatings on exposed surfaces of medical devices may flake off or otherwise be damaged during delivery, thereby preventing the biologically or pharmacologically active substance from reaching the target site. Still further, drug impregnated polymer coatings are limited in the quantity of the biologically or pharmacologically active substance to be delivered by the amount of a drug that the polymer coating can carry and the size of the medical devices. Controlling the rate of elution using polymer coatings is also difficult.

Accordingly, drug-eluting medical devices that enable increased quantities of a biologically or pharmacologically active substance to be delivered by the medical device, and allow for improved control of the elution rate of the substance, and improved methods of forming such medical devices are needed.

SUMMARY OF INVENTION

In an embodiment of a method of forming a stent, an elongated composite member including an outer member and a core member disposed within a lumen of the outer member is shaped into a stent pattern having a plurality of struts interconnected by crowns. Openings are formed through the outer member to the core member at the struts, either before or after shaping the composite member into the stent pattern. After shaping the composite member into the stent pattern, the composite member is processed such that the core member is removed from at least a plurality of the struts of the stent without adversely affecting the outer member and such that the core member is not removed from at least a plurality of the crowns of the stent, thereby leaving the outer member with a lumen in at least a plurality of the struts and the outer member with the core member in at least a plurality of the crowns. The lumens may then be filled with a biologically or pharmacologically active substance(s).

In another embodiment of a method of forming a stent, a plurality of elongated composite members, each including an outer member and a core member disposed within a lumen of the outer member, are shaped into waveforms having a plurality of struts interconnected by crowns. The waveforms are formed into a plurality of cylindrical elements. The cylindrical elements are aligned along a common longitudinal axis and joined together to form a tubular stent. Openings are formed through the outer members of the struts. After shaping the composite members into a waveform, the waveforms are processed such that the core member is removed from at least a plurality of the struts of the waveform without adversely affecting the outer member and such that the core member is not removed from at least a plurality of the crowns of the waveform, thereby leaving the outer member with a lumen in at least a plurality of the struts and the outer member with a core member in at least a plurality of the crowns. The lumens may then be filled with a biologically or pharmacologically active substance(s).

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements.

Figure 1:
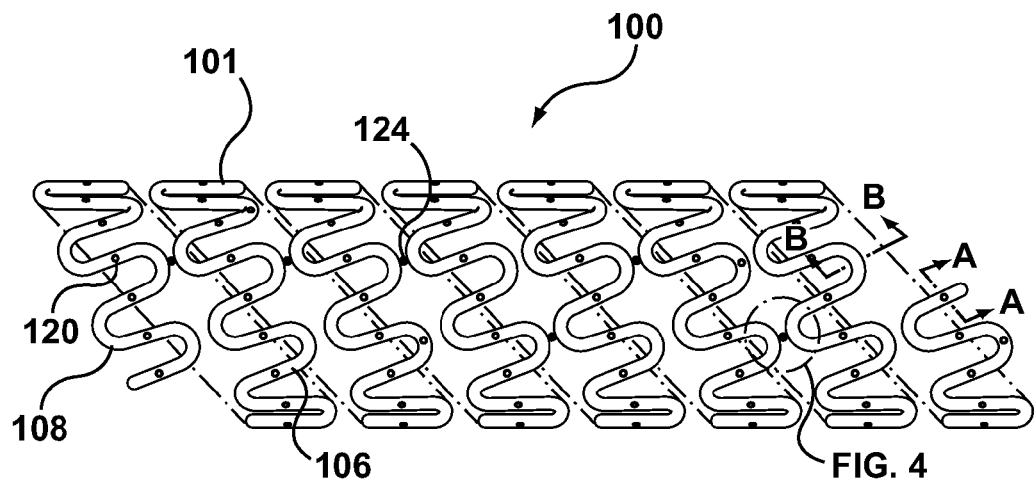
FIG. 1 is a schematic illustration of an embodiment of an exemplary stent.

An embodiment of a stent 100 disclosed herein is shown in FIGS. 1-4. In the embodiment shown in FIG. 1, stent 100 is formed from a wire 101 bent or formed into a series of generally sinusoidal waves including generally straight segments or struts 106 joined by bent segments or crowns 108 and helically wrapped into a tube, as shown in FIG. 1. The term "wire" as used herein means an elongated element or filament or group of elongated elements or filaments and is not limited to a particular cross-sectional shape or material. In the embodiment shown in FIG. 1, selected crowns 108 of longitudinally adjacent sinusoids may be joined by, for example, fusion points 124. The invention hereof is not limited to the pattern shown in FIG. 1. Stent 100 can be formed into any pattern suitable for use as a stent. For example, and not by way of limitation, stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety.

Figure 2:
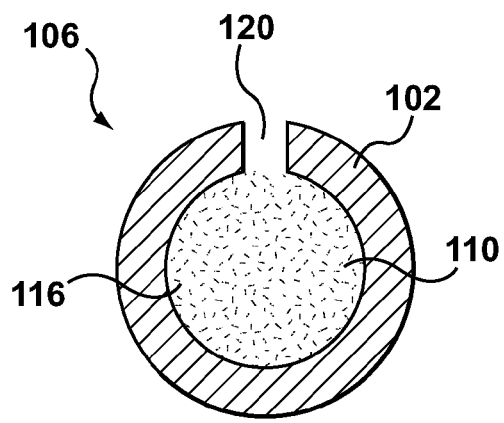
FIG. 2 is a cross-sectional view taken along line A-A of FIG. 1.
Figure 3:
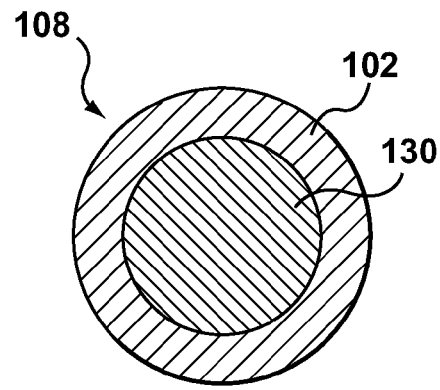
FIG. 3 is a cross-sectional view taken along line B-B of FIG. 1.
Figure 4:
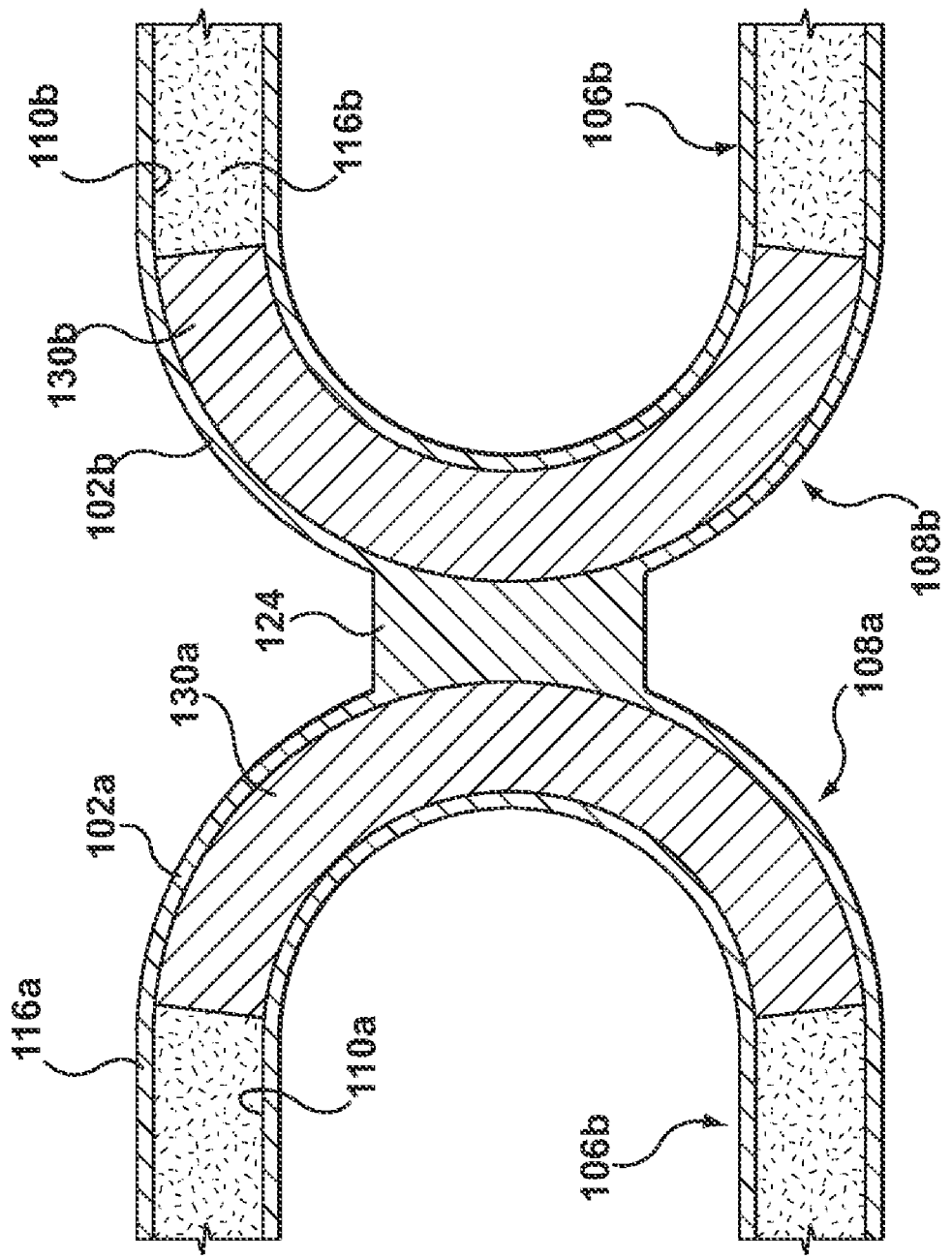
FIG. 4 is a schematic longitudinal cross section of a portion of the stent of FIG.

As shown in FIGS. 2-4, wire 101 of the completed stent 100 is hollow in the strut regions 106 (FIG. 2) and includes a core member 130 in the crown regions 108 (FIG. 3). In particular, FIG. 2 is a cross-sectional view of wire 101 taken along line A-A of FIG. 1 (at a strut 106). FIG. 3 is a cross-sectional view of wire 101 taken along line B-B of FIG. 1 (at a crown 108). FIG. 4 shows a schematic longitudinal cross section of adjacent crowns 108a, 108b fused together at a fusion point 124. As shown in FIG. 4, core member 130a, 130b is disposed within an outer member 102a, 102b for at least a portion of the crowns 108a, 108b, while outer members 102a, 102b are hollow at the struts 106a, 106b. As shown in FIGS. 2 and 4, the lumens 110 of outer members 102 at struts 106 are filled with a biologically or pharmacologically active substance 116 (116a, 116b in FIG. 4).

Openings 120 through outer member 102 at struts 106 permit biologically or pharmacologically active substance 116 to elute from lumen 110. In the embodiment shown, openings 120 are directed outwardly or toward the abluminal surface of the stent. However, openings 120 may be provided anywhere along the circumference of wire 101. Openings 120 are dispersed along the length of the stent 100 at struts 106 and through the wall of outer member 102 to permit biologically or pharmacologically active substance 116 to be released from lumens 110. Openings 120 may be sized and shaped as desired to control the elution rate of biologically or pharmacologically active substance 116 from stent 100. Larger sized openings generally permit a faster elution rate and smaller sized openings generally provide a slower elution rate. Further, the size and/or quantity of openings 120 may be varied along stent 100 in order to vary the quantity and/or rate of biologically or pharmacologically active substance 116 being eluted from stent 100 at different portions of stent 100. Openings 120 may be, for example and not by way of limitation, 5-30 μm in diameter. Openings 120 may have a constant diameter through the depth or have a tapered or conical shape.

Figure 5:
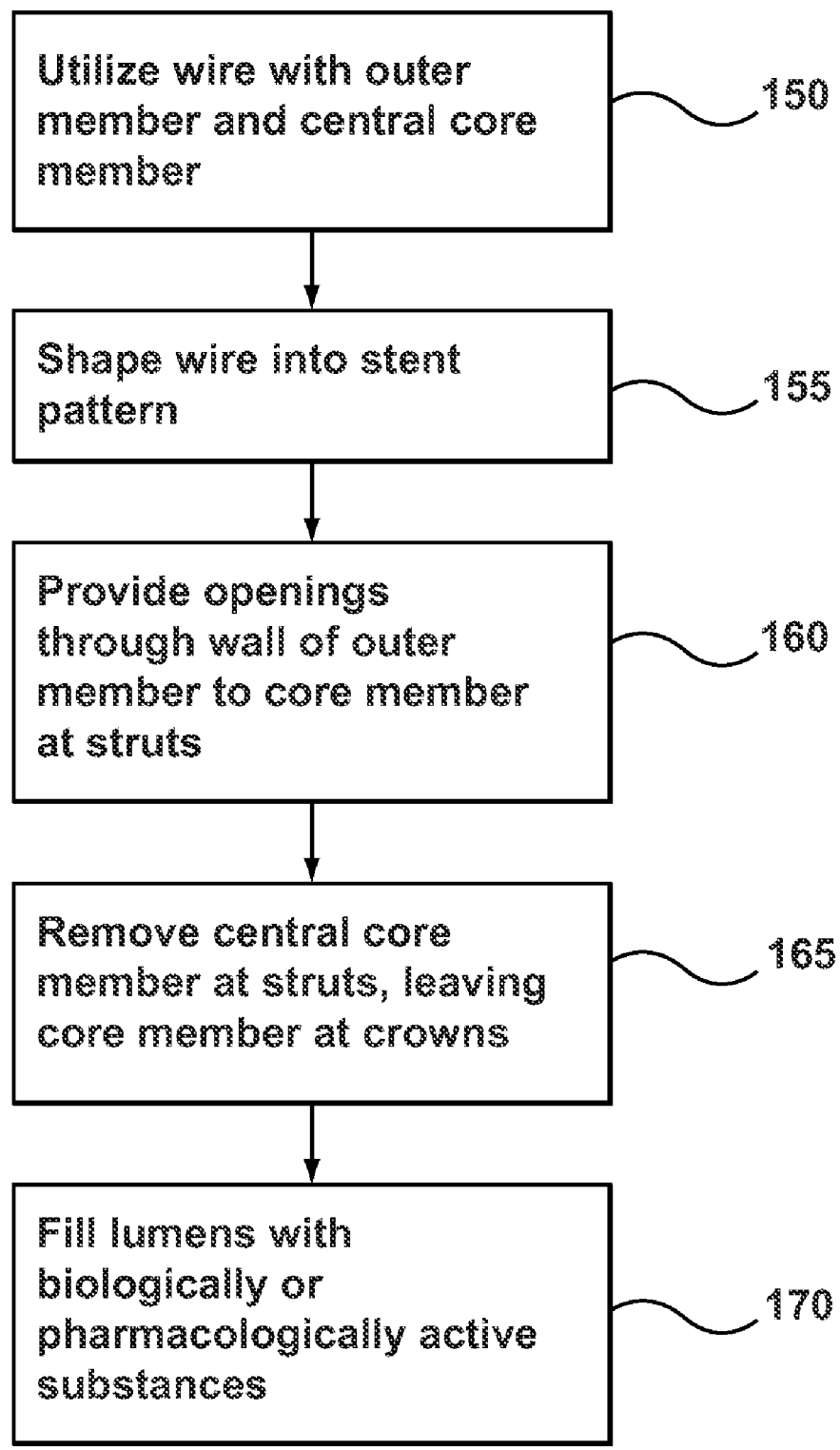
FIG. 5 is a flow chart of an embodiment of a method of forming a stent.
Figure 6:
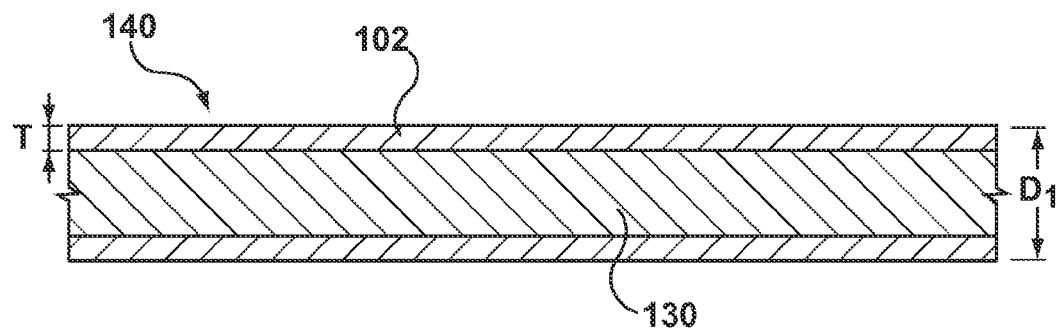
FIG. 6 is a schematic longitudinal cross-section of a core wire.

FIGS. 5-12 show schematically an embodiment of a method of making the stent 100 of FIG. 1 having the wire 101 of FIGS. 1-4. As shown in FIG. 5, step 150 is to utilize a wire with an outer member and a central core member, as shown in FIG. 6. These types of wire are sometimes referred to as core wires and may also be referred to as composite members. Core wire 140 hereof is formed of an outer member 102 and an inner or core member 130, as shown schematically in FIG. 6. Outer member 102 becomes hollow wire 102 of stent 100, and thus has been labeled with the same reference number. Core wire 140 may be formed by any method known in the art, for example and not by way of limitation, a drawn filled tubing process, extruding the outer member over the inner member, or any other suitable method. Core wires suitable for medical applications are available, for example, from Ft. Wayne Metals of Ft. Wayne, Ind.

Outer member 102 can be any material that is suitable to be used as a stent. Outer member 102, as explained in more detail below, is the surviving material that will become hollow wire 102. For example and not by way of limitation, outer member 102 may be a stainless steel, "MP35N", "MP20N", nickel titanium alloys such as Nitinol, magnesium, L605, or combinations thereof. "MP35N" and "MP20N" are trade names for alloys of cobalt, nickel, chromium and molybdenum available from Standard Press Steel Co., Jenkintown, Pa. "MP35N" generally consists of 35% cobalt, 35% nickel, 20% chromium, and 10% molybdenum. "MP20N" generally consists of 50% cobalt, 20% nickel, 20% chromium, and 10% molybdenum. The requirements for the material of outer member 102 are that it be biocompatible, sufficiently resilient to be used as a stent, and that it survive the process for eliminating core member 130, as discussed in more detail below.

Core member 130 may be a material that provides sufficient support to outer member 102 while the core wire is being bent into the stent pattern, as explained in more detail below. Core member 130 may be made of a material that is more radiopaque than the material of outer member 102 such that the remaining core member material can be seen by a practitioner. Further, core member 130 is made of a sacrificial material that can be removed by a process that does not damage the material of outer member 102. Examples of materials for core member 130 include, but are not limited to, tantalum (Ta), tungsten (W), molybdenum (Mo), niobium (Nb), rhenium (Re), carbon (C), germanium (Ge), silicon (Si) and alloys thereof.

As shown in FIG. 6, outer member 102 may have an outer diameter $D_1$ in the range of 0.002 inch to 0.010 inch and a wall thickness T in the range of 0.0005 inch or larger. The values listed above are merely examples and other diameters and wall thicknesses may be used depending on, for example, the material used, the desired stent shape, the target location, the amount of biologically or pharmacologically active substance to be eluted, and other factors known to those skilled in the art.

Figure 7:
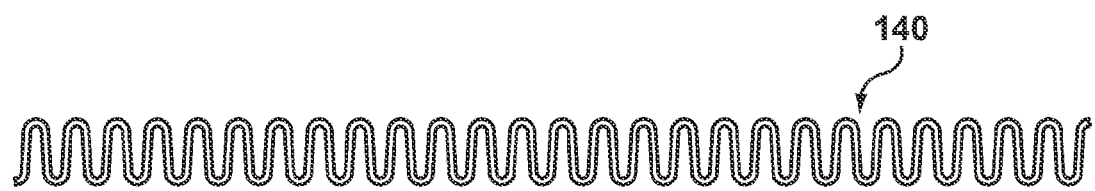
FIG. 7 illustrates a portion of a core wire formed into a two dimensional waveform.
Figure 8:
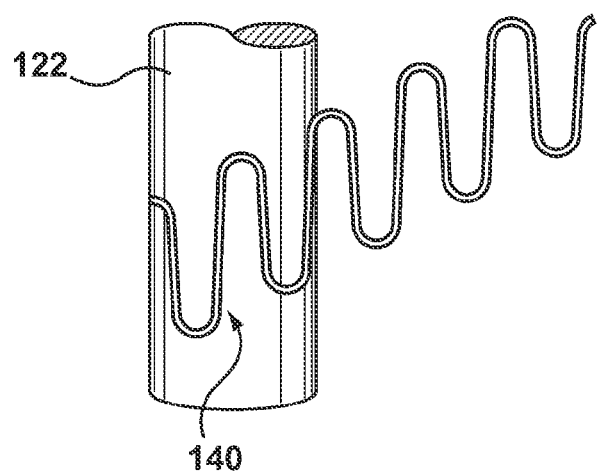
FIG. 8 illustrates a waveform such as the waveform of FIG. 7 being wrapped around a mandrel.

Referring to FIG. 5, step 155 is to shape the core wire 140 into the stent pattern. As discussed above, the stent pattern can be the pattern shown in FIG. 1 or any other suitable pattern formed from a wire. Further, although the order of all the steps is not critical, step 155 should be done prior to removing core member 130 (i.e., step 165 explained in more detail below). Shaping core wire 140 into the stent pattern while core member 130 is disposed within outer member 102 helps prevent kinking or other deformations from occurring in outer member 102 or lumen 110. Shaping the core wire 140 into the stent pattern shown in FIG. 1 generally includes the steps of forming core wire 140 into a two dimensional waveform, as shown in FIG. 7, followed by wrapping the waveform around a mandrel 122, as shown in FIG. 8. The end result is a helical stent pattern formed onto a mandrel 122. Selected crowns 108 of the helical pattern may then be fused or laser fused together and the stent may be removed from the mandrel. Methods for forming core wire 140 into a waveform may include, but are not limited to, the methods described in U.S. application Ser. No. 12/428,581, filed Apr. 23, 2009, which is incorporated by reference herein in its in entirety, or passing the core wire through gears such as those disclosed in U.S. Pat. No. 2,153,936 issued to Owens et al., which is also incorporated by reference herein in its entirety. Other methods for forming a wire into a waveform and for helically wrapping the waveform into a tube may be used, as known to those skilled in the art.

Figure 9:
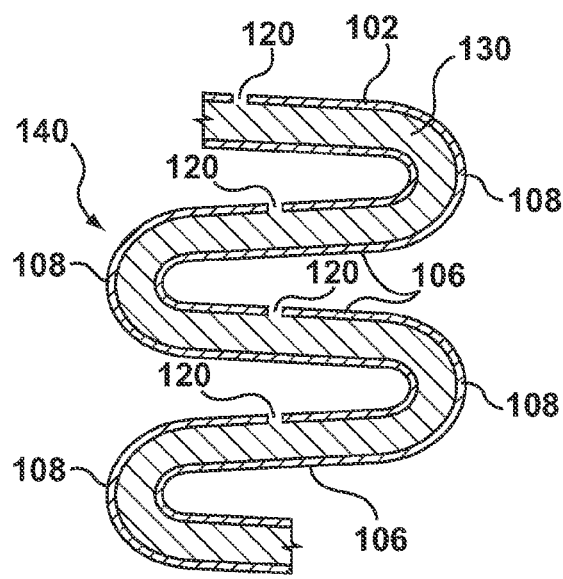
FIGS. 9-12 are schematic side cross-sectional views of a portion of a core wire illustrating the core wire at stages of the method of FIG. 5.

Step 160 shown in FIG. 5 is to provide openings 120 through outer member 102. Openings 120 may be laser cut, drilled, etched, or otherwise provided through outer member 102. Step 160 need not be performed after step 155, nor before step 165, although in some instances it is preferred to be before step 165, as explained in more detail below. If step 160 is performed after step 155, FIG. 9 shows a schematic side cross-sectional view of a portion of core wire 140 with openings 120 disposed through outer member 102 at struts 106. Core member 130 is disposed within outer member 102 throughout the length of core wire 140.

Step 165 is to etch away core member 130 at struts 106. Step 165 can be performed by any suitable process for removing core member 130 while preserving outer member 102. In particular, if outer member 102 is made from MP35N and core member 130 is made from tantalum, subjecting core wire 140 to xenon difluoride ($XeF_2$) gas at low pressure (1-6 Torr) and relatively high temperature (approximately 110°-150° C.) causes the xenon difluoride ($XeF_2$) gas to react with the tantalum (Ta) core member 130 to form $TaF_5$ and Xe gases, which can be exhausted from lumens 110. Xenon difluoride ($XeF_2$) gas reacts similarly with a core member 130 made from tungsten, molybdenum, niobium, rhenium, carbon, germanium, and silicon. However, xenon difluoride ($XeF_2$) gas does not react with an outer member 102 formed of MP35N. Other examples of suitable outer member/core member combinations and methods for removing core members are described in co-pending U.S. application Ser. No. 12/500,359, filed Jul. 9, 2009 and co-pending U.S. application Ser. No. 12/884,551 filed Sep. 17, 2010, each of which is incorporated by reference herein in its entirety. For example, and not by way of limitation, methods such as wet chemical dissolution, solubilization, sublimation, and melting may be used with appropriate outer member/core member combinations.

Figure 10:
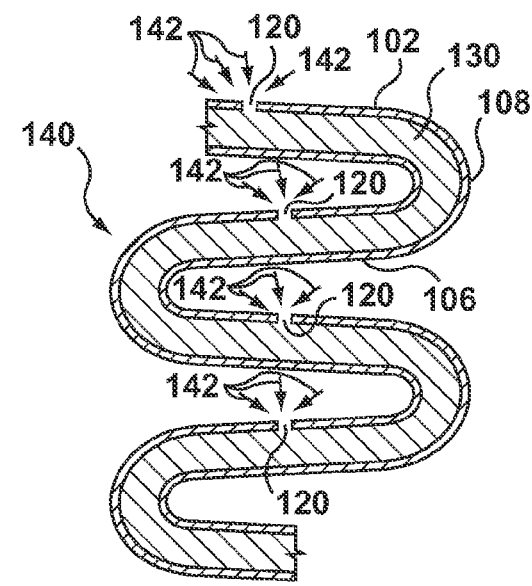
Figure 11:
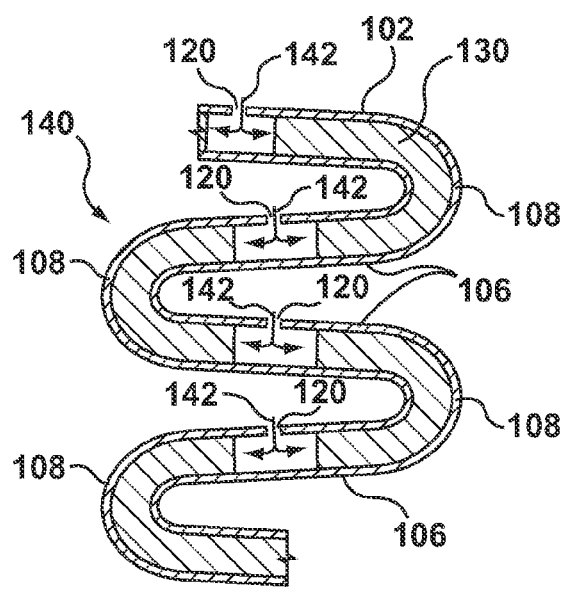
Figure 12:
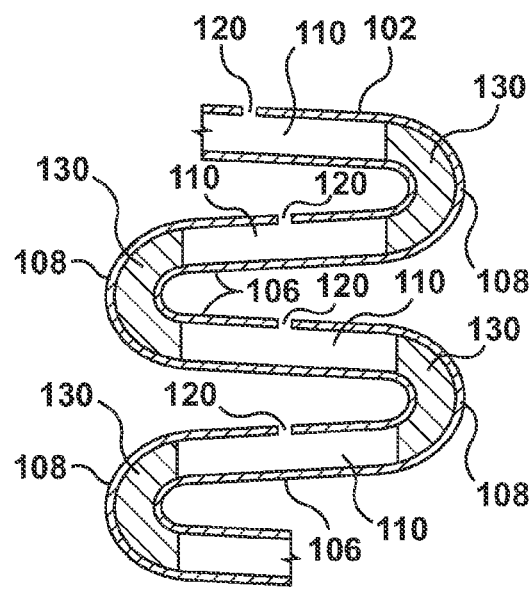

FIGS. 10-12 show schematically step 165 of FIG. 5. In particular, FIG. 10 shows a portion of core wire 140 exposed to the etchant, represented by arrows 142. Although arrows 142 are shown generally at openings 120, those skilled in the art recognize that the core wire 140 may generally be placed in an environment with the etchant surrounding the core wire 140. The etchant does not harmfully affect outer member 102, but begins to etch away core member 130 through openings 120, as shown in FIG. 11. Because openings 120 are located in the strut regions 106, the etchant etches core member 130 starting at openings 120 and working towards crowns 108, as shown in FIG. 11. Parameters of the step of exposing core wire 140 to the etchant are controlled such that the desired amount of core member 130 is removed from outer member 102. For example, and not by way of limitation, parameters such as time of exposure to the etchant, pressure, size and location of openings 120, and other parameters affecting the removal of core wire 140 may be controlled such that the desired amount of core member 130 is removed from outer member 102.

In the present embodiment, portions of core member 130 at crowns 108 remain after step 165. In an embodiment, ends of core wire 140 are capped or otherwise covered such that access to core member 130 by the etchant (such as xenon difluoride) is through openings 120. In a non-limiting example, a core wire 140 formed into the stent pattern is placed in a Xetch® Xenon Difluoride Etching System model e1, available from XACTIX, Inc. In a non-limiting example, a core wire 140 with an MP35N outer member 102 with an outer diameter of 0.002 to 0.01 inch, and a wall thickness of at least 0.0005 inch, a tantalum core member 130 having a diameter of at least 0.004 inch, is placed in a Xetch® Xenon Difluoride Etching System model e1 machine. The expansion chamber is filled with 8 torr of $XeF_2$ gas. A valve to the process chamber is opened such that the pressure in the process chamber will be less than 8 torr. In this particular example, all of core member 130 may be removed using 30 cycles of 30 seconds each at 110° C. for the process chamber. In order to remove core member 130 only at struts 106, the number of cycles or duration of the cycles may be reduced. For example, cycles in the range of 5 to 29 would remove part of the core member 130 but not the entire core member 130.

Figure 13:
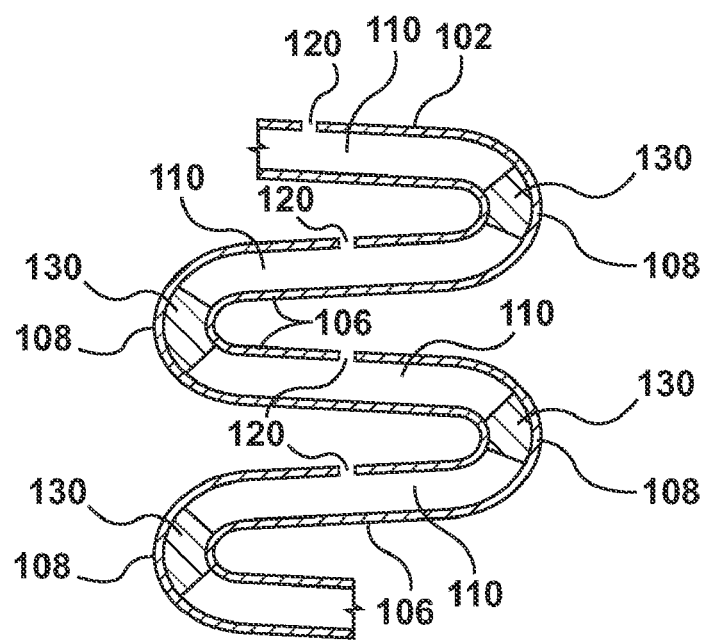
FIG. 13 is a schematic side cross-sectional view of a portion of a stent with the core member removed from the struts and portions of the crowns thereof.

The parameters may be varied depending on the size of the core member 130, the length of the struts 106, the amount of the core member 130 that is to be removed, the size, number and location of openings 120, and other factors known to those skilled in the art. For example, the amount of core member 130 remaining at crowns 108 may be varied. Core member 130 may remain only at a small portion of crowns 108, as shown in FIG. 13, or a large portion of crowns 108, as shown in FIG. 12. For example, and not by way of limitation, core member 130 occupying 5% to 100% of the volume of lumen 110 of crowns 108 may remain. With other factors remaining equal, core wire 140 would be exposed to the etchant for more cycles or longer cycles such that more of core member 130 is removed to result in the embodiment of FIG. 13 versus the embodiment of FIG. 12. Similarly, if there are two or more openings 120 per strut 106, rather than one opening 120 shown in FIGS. 9-12, the number of cycles or time per cycle can be adjusted to etch the desired amount of core member 130.

Accordingly, after step 165 is completed, outer member 102 remains and core member 130 has been removed from the struts 106, leaving the structure shown in FIG. 12 (or FIG. 13). As noted above, openings 120 do not need to be formed prior to the step of removing core member 130 provided there is a way to expose core member 130 to the etchant such that the core member may be removed at the struts without removing core member 130 at the crowns 108. For example, and not by way of limitation, temporary ports may be formed through outer member 102 to expose core member 130 to the etchant.

After core member 130 has been removed from the strut regions, a biologically or pharmacologically active substance 116 may be injected into lumen 110, as shown in step 170 of FIG. 5. This produces a hollow wire or outer member 102 with biologically or pharmacologically active substance 116 disposed in lumens 110 at struts 106, and openings 120 through which biologically or pharmacologically active substance 116 may be eluted, as shown FIGS. 2-4. Lumen 110 may be filled with biologically or pharmacologically active substance 116 by the methods described in co-pending U.S. application Ser. Nos. 12/884,503; 12/884,578; 12/884,362; 12/884,451; 12/884,596; and Ser. No. 12/884,501 all of which were filed on Sep. 17, 2010, each of which is incorporated by reference herein in its entirety, or any other suitable method known to those skilled in the art.

Leaving core member 130 in at least a portion of crowns 108 may be desirable for several reasons. For example, and not by way of limitation, using a radiopaque material for core member 130 and leaving core member 130 in crowns 108 may make it easier to visualize the stent during delivery and placement at a treatment site. Further, leaving core member 130 at the crowns 108 may provide additional support for fusing crowns in adjacent windings to each other, or may allow such fusing to take place after filling the lumens 110 with a biologically or pharmacologically active substance. Further, leaving core member 130 at crowns 108 divides lumen 110 into multiple lumens. Accordingly, some lumens may be filled with a first biologically or pharmacologically active substance and other lumens may be filled with a second biologically or pharmacologically active substance that is different from the first biologically or pharmacologically active substance. For example, and not by way of limitation, some lumens may have openings 120 directed to an abluminal side of the stent and be filled by an anti-proliferative agent while other lumens may have openings 120 directed to a luminal side of the stent and be filled with an antithrombotic agent. In another non-limiting example, different lumens may be configured to release the same biologically or pharmacologically active substance at different times in vivo, such as by varying the size of the openings 120, using an additive, a biodegradable liner or plug, or other time release mechanisms know to those skilled in the art. Other combinations of biologically or pharmacologically active substances may be utilized, as known to those skilled in the art.

It is also possible to leave core member 130 in some of the crowns 108 of the stent while removing core member 130 from other crowns 108 of the stent. For example, and not by way of limitation, the first winding and last winding of the stent may include the core member 130 at the crowns 108, while the remaining middle windings would not include the core member 130 at the crowns 108. Such an embodiment may be accomplished by adding openings 120 at the crowns 108 where the core member 130 is to be removed prior to exposing the stent to the etchant. Thus, core member 130 will be removed from the crowns 108 with openings 120, but not the crowns 108 without openings 120. Those skilled in the art may do this for several reasons. For example, and not by way of limitation, leaving radiopaque material at crown(s) at proximal and distal ends of the stent may provide better visualization of the boundaries of the stent, rather than leaving radiopaque material at all of the crowns. In another example, it may be desirable to have a higher dosage of biologically or pharmacologically active substance in the middle portion of the stent and a lower dosage of biologically or pharmacologically active substance at the ends of the stent. Other variations of crowns with or without the core member may be desirable for various reasons known to those skilled in the art.

Figure 14:
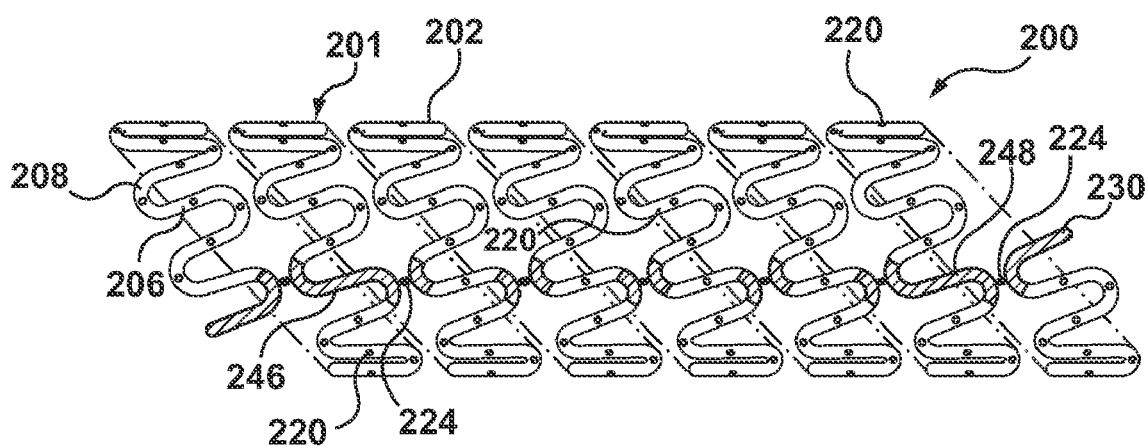
FIG. 14 is a schematic view of an embodiment of a stent.

FIG. 14 shows schematically an embodiment of a stent 200 with a core member 230 remaining in some of the crowns 208 and being removed from the struts 206 and some of the crowns 208. In the embodiment shown in FIG. 14, core member 230 is maintained at fusion locations 224 between adjacent windings of the helically wrapped stent. In a non-limiting example of a method of forming such a stent, the method described above is used except that openings 220 are provided at the crowns where the core member is to be removed. Further, at the ends of the stent, and at locations 246, 248, core member 230 may remain at some of the struts 206 of the stent 200. For example, in the embodiment shown in FIG. 14, the proximity of some crowns with the core member remaining may make it desirable to keep the core member in the struts there between, as shown at locations 246, 248. In an embodiment such as the one shown in FIG. 14, one skilled in the art may load different windings of the stent with different biologically or pharmacologically active substances. For example, and not by way of limitation, some of the windings may have openings 220 to the luminal side of the stent with a first biologically or pharmacologically active substance disposed in the lumens 210 thereof and other windings may have openings 220 to the abluminal side of the stent with a second biologically or pharmacologically active substance disposed in the lumens 210 thereof.

Figure 15:
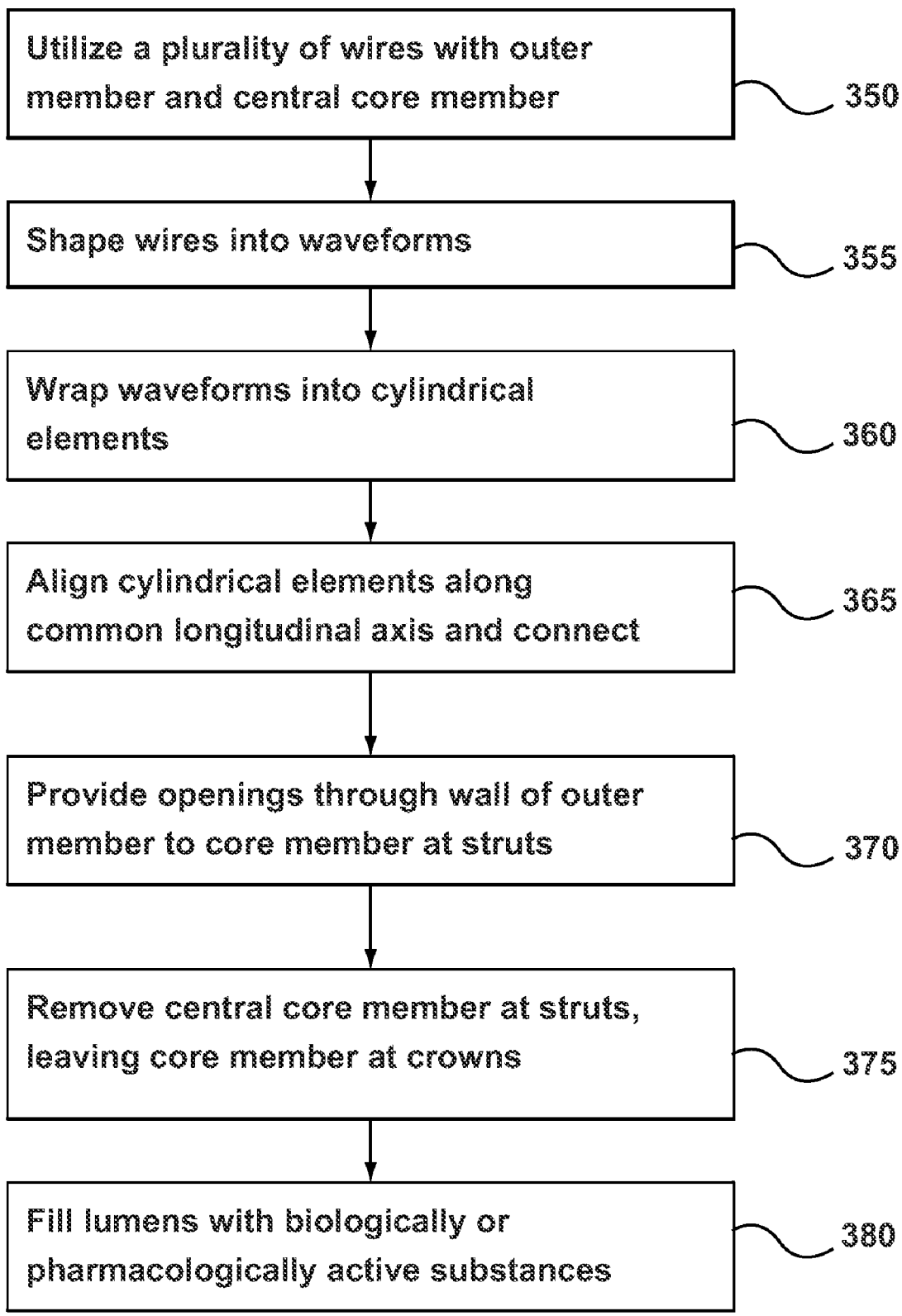
FIG. 15 is a flow chart of an embodiment of a method of making a stent.
Figure 16:
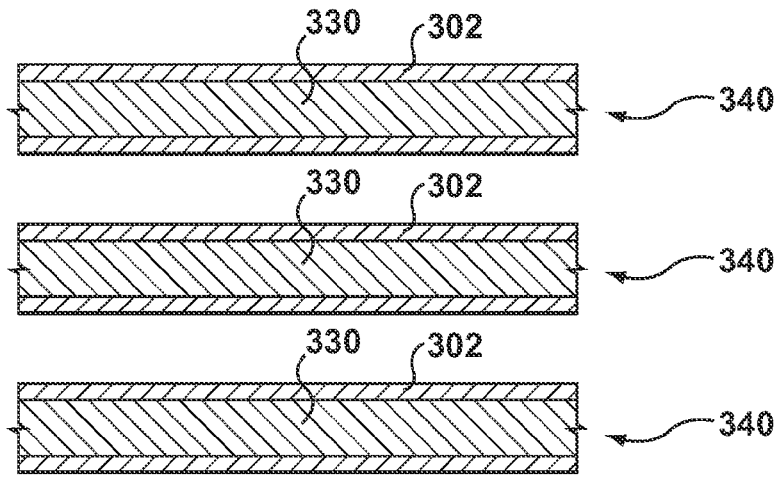
FIG. 16 is a schematic longitudinal cross-section of a plurality of core wires.

FIG. 15 is a flow chart of another embodiment of a method of making a stent. As shown in FIG. 15, step 350 is to utilize a plurality of core wires 340 with an outer member 302 and a central core member 330, as shown in FIG. 16. Core wires 340 may be as described above for core wire 140. For further description of core wires 340, including the description of outer member 302 and core member 330, the description of core wire 140 above is incorporated herein. FIG. 16 shows three core wires 340. Those skilled in the art would recognize that the number of wires used can vary and may depend on the number of cylindrical elements (described below) desired for the stent.

Figure 17:
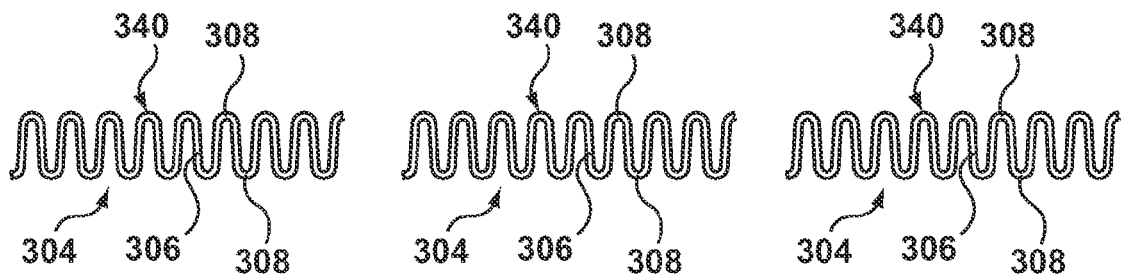
FIG. 17 illustrates a plurality of core wires formed into a two dimensional waveform.
Figure 18:
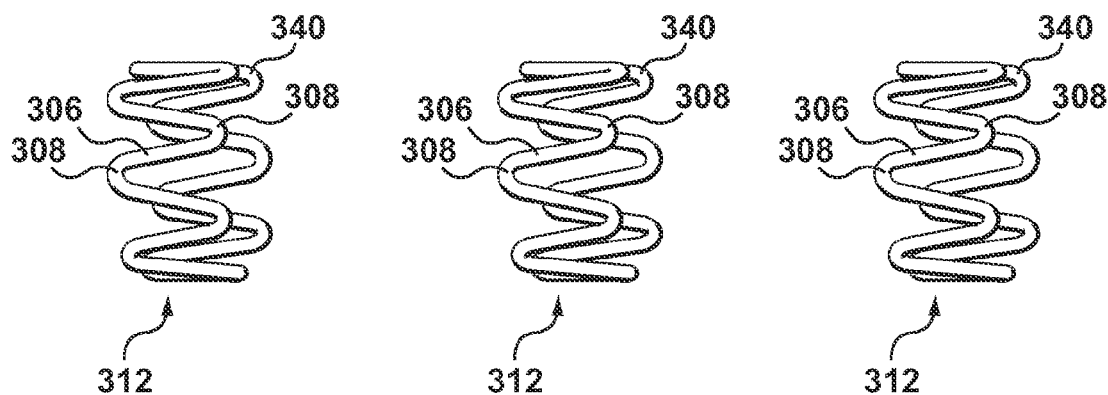
FIG. 18 illustrates the waveforms of FIG. 17 wrapped into cylindrical elements.
Figure 19:
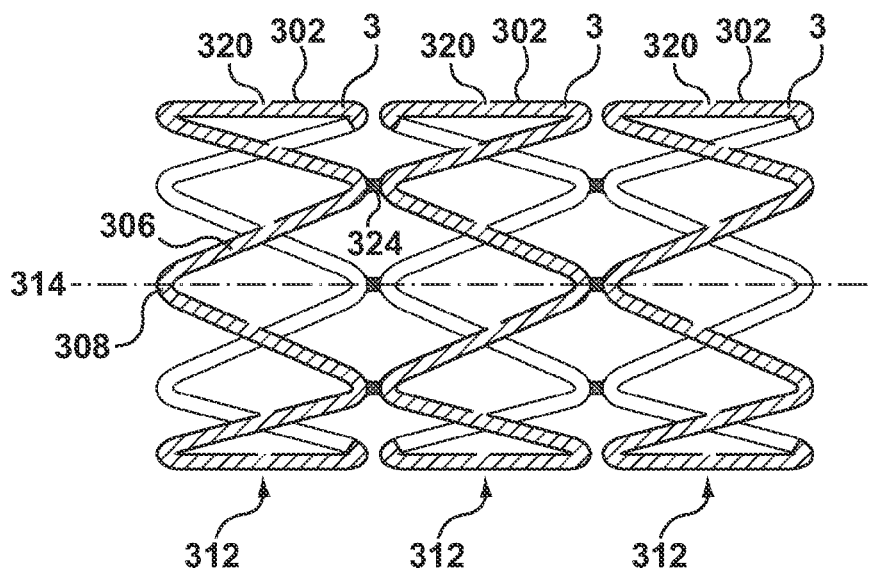
FIGS. 19-21 are schematic illustrations of a stent illustrating the stent at stages of the method of FIG. 15.

Referring to FIG. 15, step 355 is to shape each core wire 340 into a two-dimensional waveform 304 having struts 306 interconnected by crowns 308, as shown, for example, in FIG. 17. Step 360 is to form each waveform 304 into a cylindrical element 312, as shown in FIG. 18. Step 365 is to align the cylindrical elements 312 along a common longitudinal axis 314 and to connect the cylindrical elements 312 together, such as by fusion or laser fusion. FIG. 19 shows cylindrical elements 312 aligned along longitudinal axis 314 and fused to each other at fusion points 324. FIG. 19 also shows openings 320 formed through outer member 302, as described in step 370. Openings may be similar to openings 120 described above. Further, openings 320 in FIG. 19 are formed only in struts 306. As described above with respect to the FIG. 14, the location of openings 320 may be varied depending on which areas of the stent will include a biologically or pharmacologically active substance, which areas will have the core member 330 removed, and other factors known to those skilled in the art.

Figure 20:
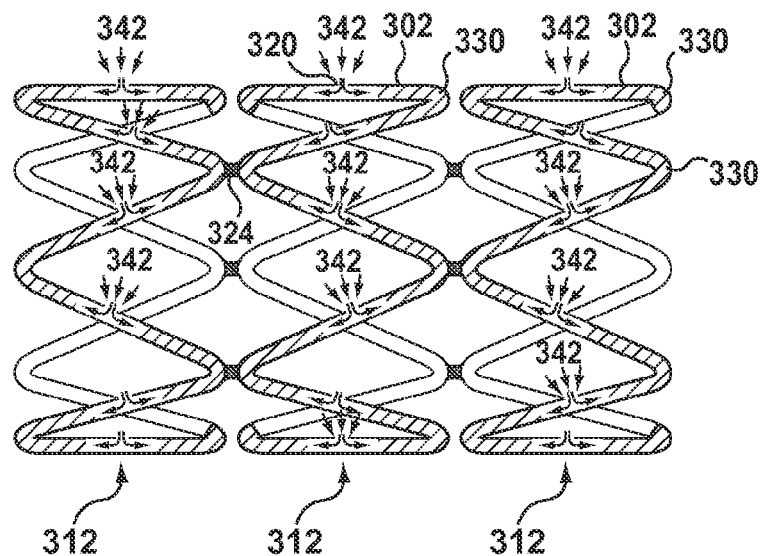
Figure 21:
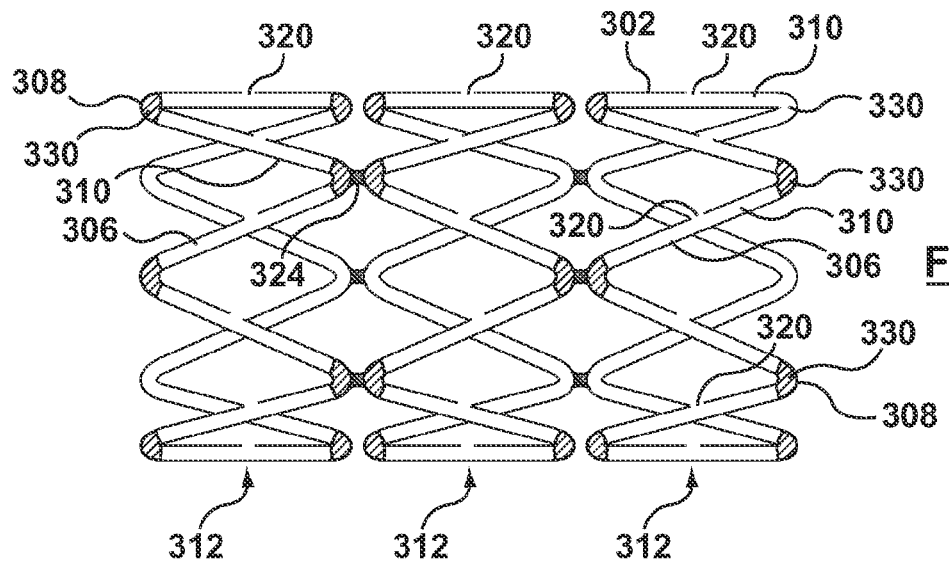

Step 375 is to etch away core member 330 at struts 306. Step 375 can be performed by any suitable process for removing core member 330 while preserving outer member 302, such as those described and incorporated by reference above. FIG. 20 shows stent 300 exposed to an etchant, represented by arrows 342. Although arrows 342 are shown generally at openings 320, those skilled in the art recognize that stent 300 may generally be placed in an environment with the etchant surrounding it. The etchant does not harmfully affect outer member 302, but begins to etch away core member 330 through openings 320, as shown in FIG. 20. Because openings 320 are located in the strut regions 306, the etchant etches core member 330 starting at openings 320 and working towards crowns 308, as shown in FIG. 20. Parameters of the step of exposing stent 300 to the etchant are controlled such that the desired amount of core member 330 is removed from outer member 302, as described above. In the present embodiment, portions of core member 330 at crowns 308 remain after step 375. Accordingly, after step 375 is completed, outer member 302 remains and core member 330 has been removed from the struts 306, leaving the structure shown in FIG. 21. As noted above, openings 320 do not need to be formed prior to the step of removing core member 330 provided there is a way to expose core member 330 to the etchant such that the core member 330 may be removed at the struts 306 without removing core member 330 at the crowns 308.

After core member 330 has been removed from the strut regions, a biologically or pharmacologically active substance may be injected into lumens 310, as shown in step 380 of FIG. 15. This produces a hollow wire or outer member 302 with a biologically or pharmacologically active substance disposed in lumens 310 at struts 306, and openings 320 through which the biologically or pharmacologically active substance may be eluted. Lumens 310 may be filled with the biologically or pharmacologically active substance by the methods described and incorporated by reference above.

Figure 22:
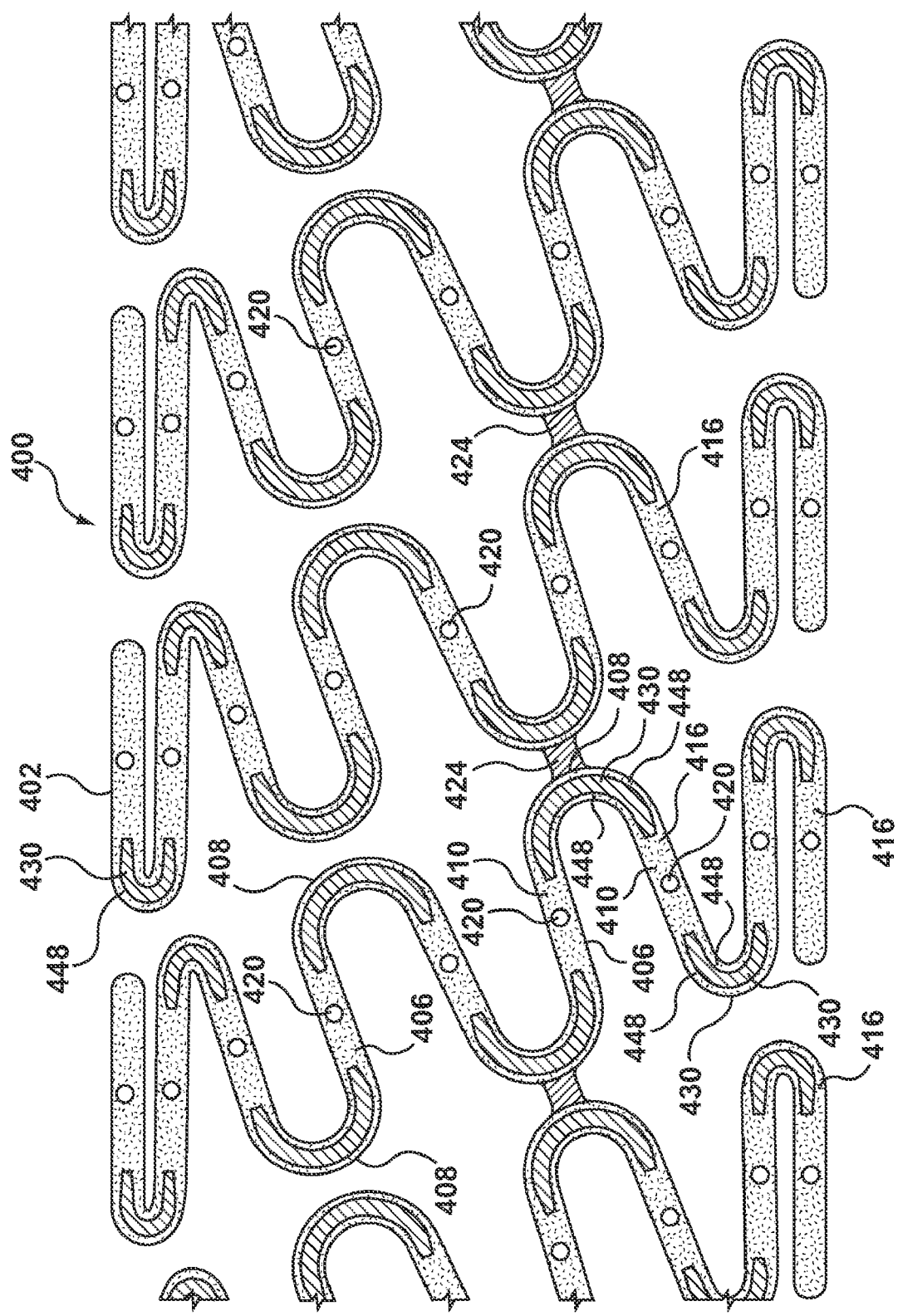
FIG. 22 is a schematic view of another embodiment of a stent.

FIG. 22 illustrates schematically a portion of an embodiment of a stent 400. Similar to the embodiments described above, stent 400 includes a wire 401 bent or formed into a series of generally sinusoidal waves including generally straight segments or struts 406 joined by bent segments or crowns 408 and helically wrapped into a tube. It is understood that the embodiment of FIGS. 15-21, with cylindrical elements attached along a common longitudinal axis, could be utilized as well.

Figure 28:
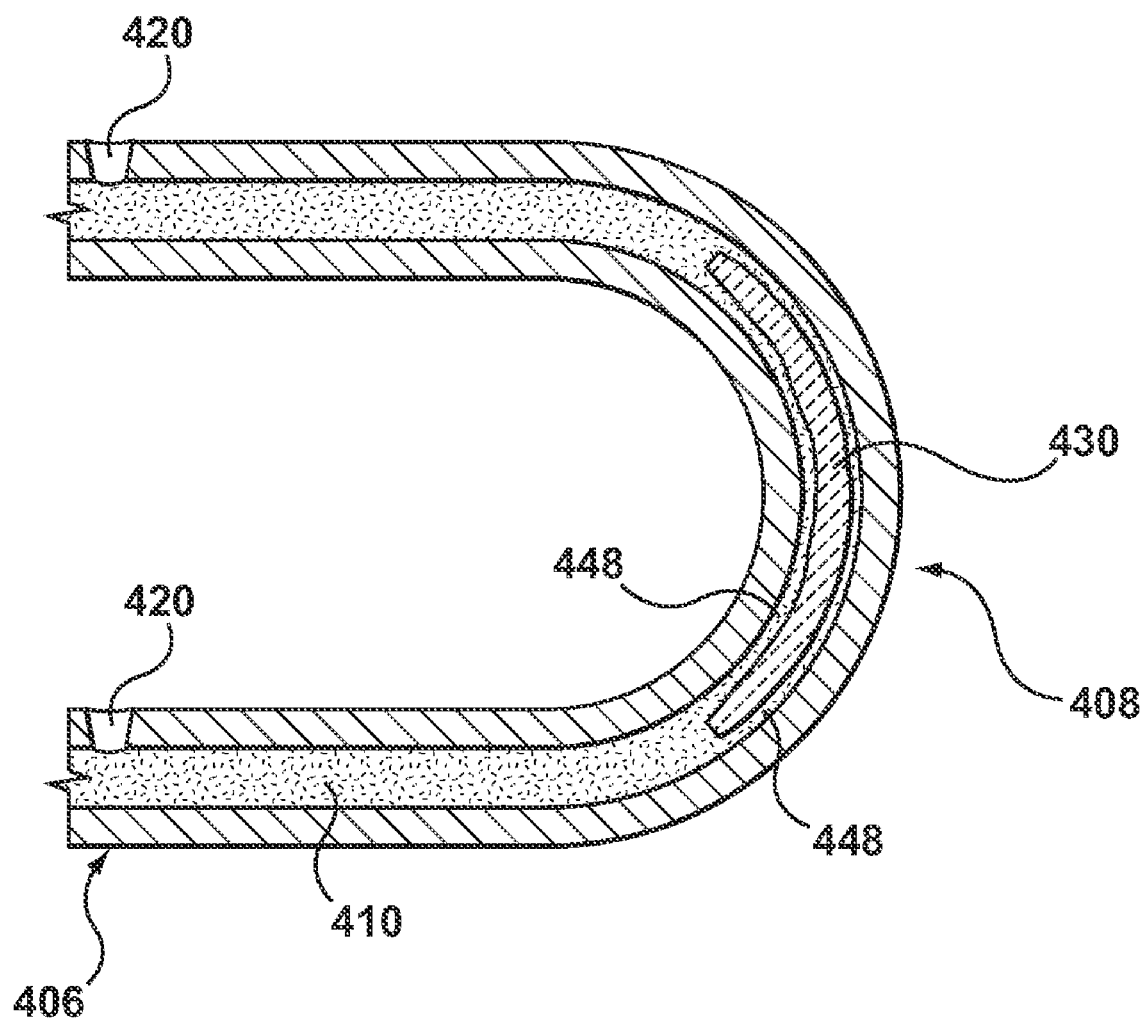

Wire 401 of stent 400 is hollow in the strut regions 406 such that wire 401 includes a lumen 410 in the strut regions 406. A core member 430 is disposed within wire 401 at the crown regions 408, as shown in FIGS. 22 and 28. Further, core member 430 does not fully occupy lumen 410 of outer member 402, even at crowns 408, such that a lumen or lumens 448 connect lumens 410 of adjacent struts 406 together through crowns 408. As shown in FIGS. 22 and 28, the lumen 410 of outer member 402 at struts 406 and lumens 448 disposed between core member 420 and outer member 402 and crowns 408 are filled with a biologically or pharmacologically active substance 416.

Openings 420 through outer member 402 at struts 406 permit biologically or pharmacologically active substance 416 to elute from lumens 410/448. Openings 420 may be the same or similar to openings 120 described above.

Figure 23:
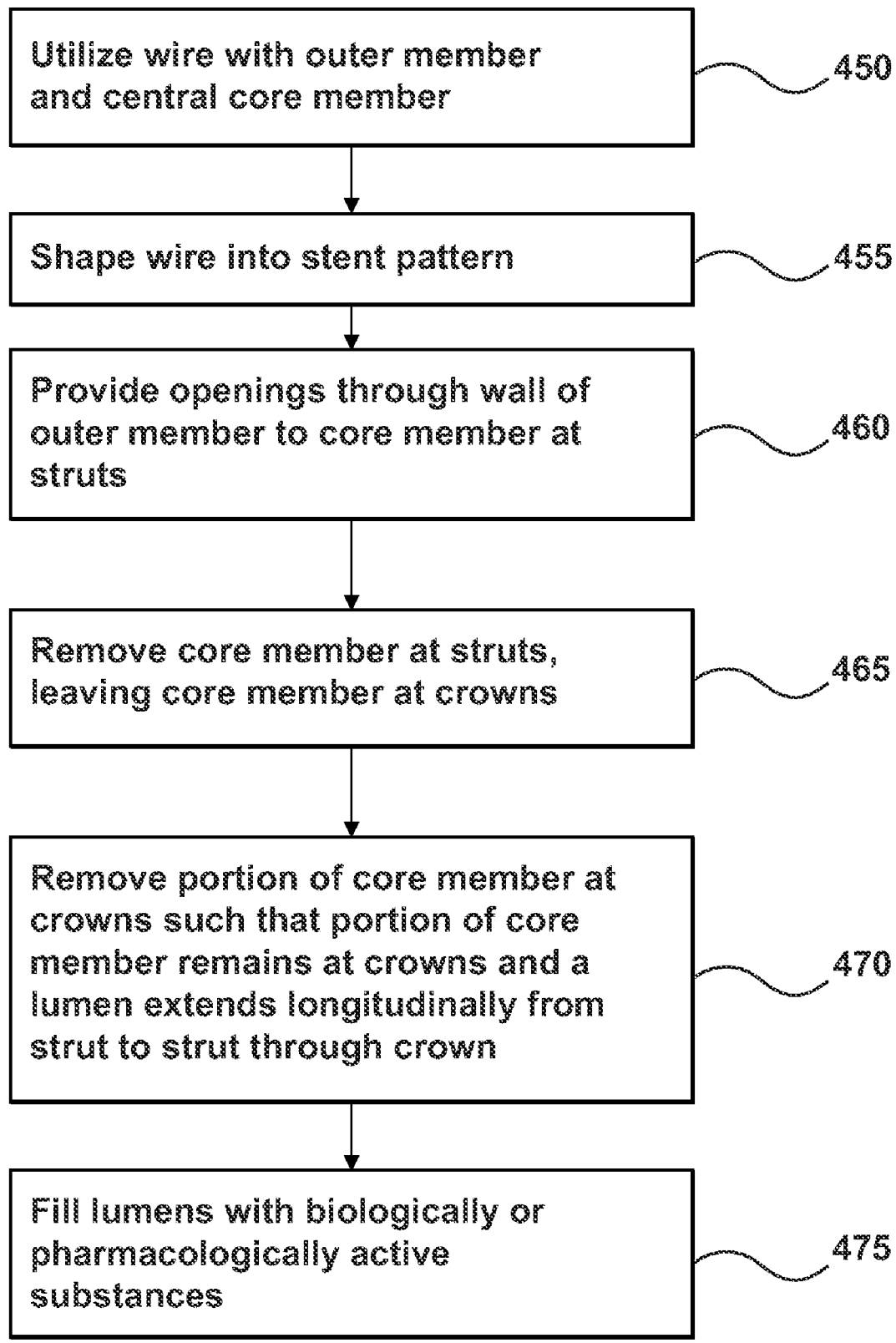
FIG. 23 is a flow chart of an embodiment of a method of making the stent of FIG. 22.
Figure 24:
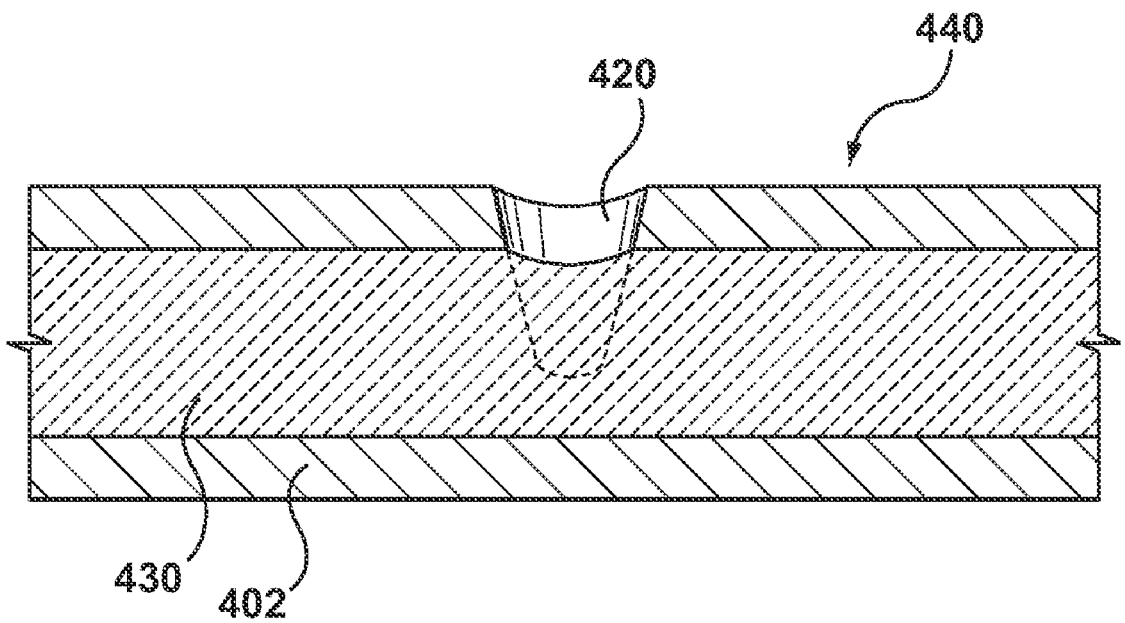
FIGS. 24 and 25 are schematic longitudinal cross-sections of a portion of a stent adjacent an opening showing a step in the method of FIG. 23.

FIG. 23 is a chart illustrating an embodiment of a method of making stent 400. Step 450 is to utilize a wire with an outer member and a central core member. Such a wire may be the core wire 140 described above. A portion of such a core wire 440 is shown in FIG. 24, including an outer member 402 and a core member 430. FIG. 24 also shows an opening 420, which is formed through outer member 402 in step 460, which may occur before or after step 455, as described above.

Referring to FIG. 23, step 455 is to shape the core wire 440 into the stent pattern. As discussed above, the stent pattern can be the pattern shown in FIG. 1 or any other suitable pattern formed from a wire, or may be a series of cylindrical elements formed from a plurality of wires, as described with respect to FIGS. 15-21. Further, although the order of all the steps is not critical, step 455 should be done prior to removing core member 430. Shaping the core wire 440 into the stent pattern shown in FIG. 22 generally includes the steps described in the embodiments above. The end result is a helical stent pattern formed onto a mandrel. Selected crowns 408 of the helical pattern may then be fused or laser fused together and the stent may be removed from the mandrel.

Step 465 is to etch away core member 430 at struts 406. Step 465 can be performed by any suitable process for removing core member 430 while preserving outer member 402, as discussed in detail above with respect to step 165.

Figure 26:
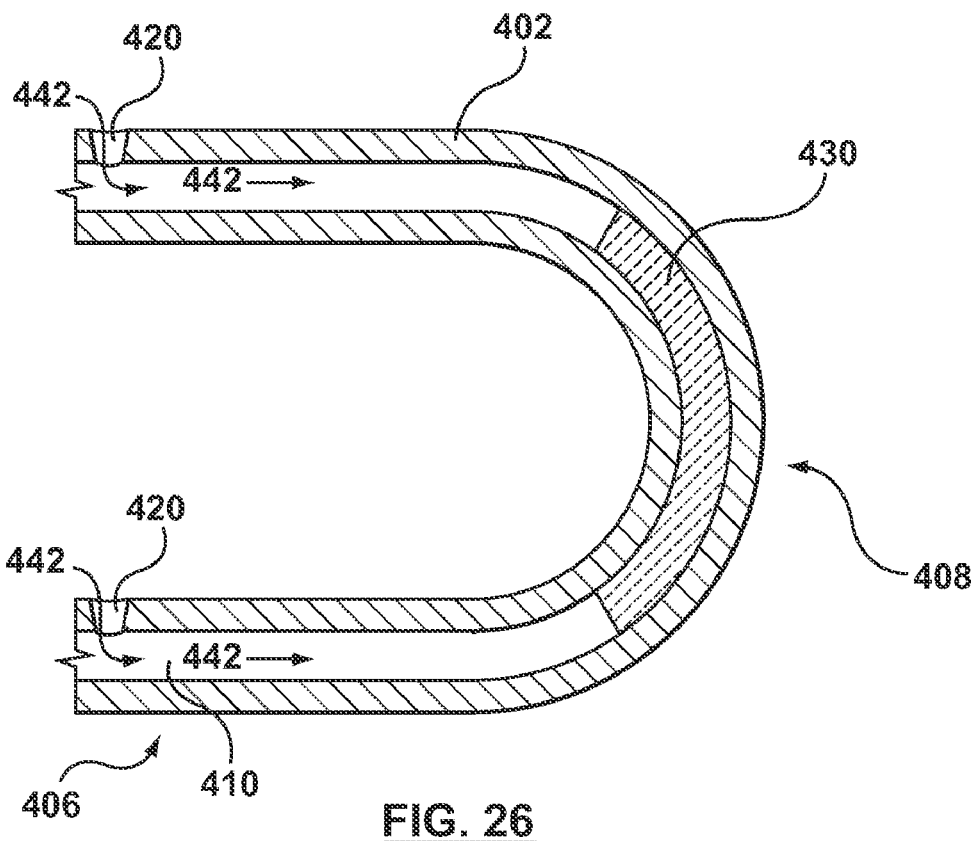
FIGS. 26-28 are schematic longitudinal cross-sections showing a crown of a stent showing a step of the method of FIG. 23.
Figure 27:
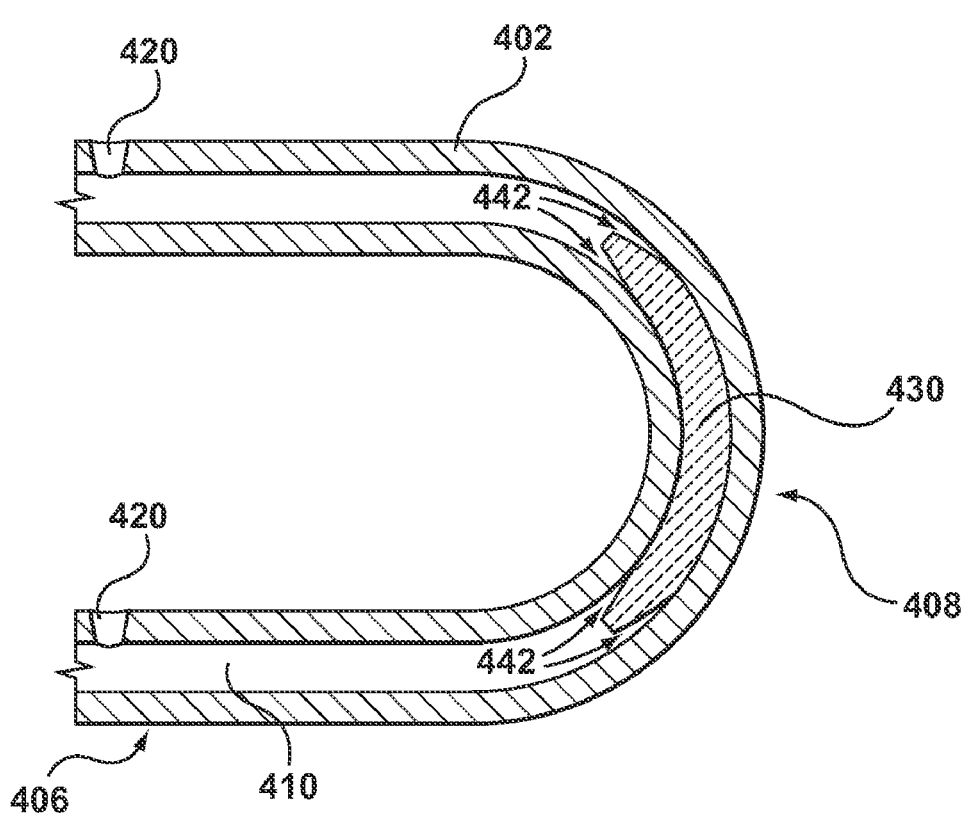

After step 465 has been completed, struts 406 include outer member 402 with lumen 410 and crowns 408 include outer member 402 with core member 430 disposed in lumen 410, as shown in FIG. 26. Step 470 is to remove a portion of core member 430 at crowns 408 such that a portion of core member 430 remains at crowns 408 and a lumen or lumens 448 extend from lumen 410 at a strut 406 to lumen 410 in an adjacent strut 406 through crown 408. Lumen 448 is part of lumen 410 of outer member 402, but has been labeled differently to distinguish it from the lumens at struts 406.

Figure 25:
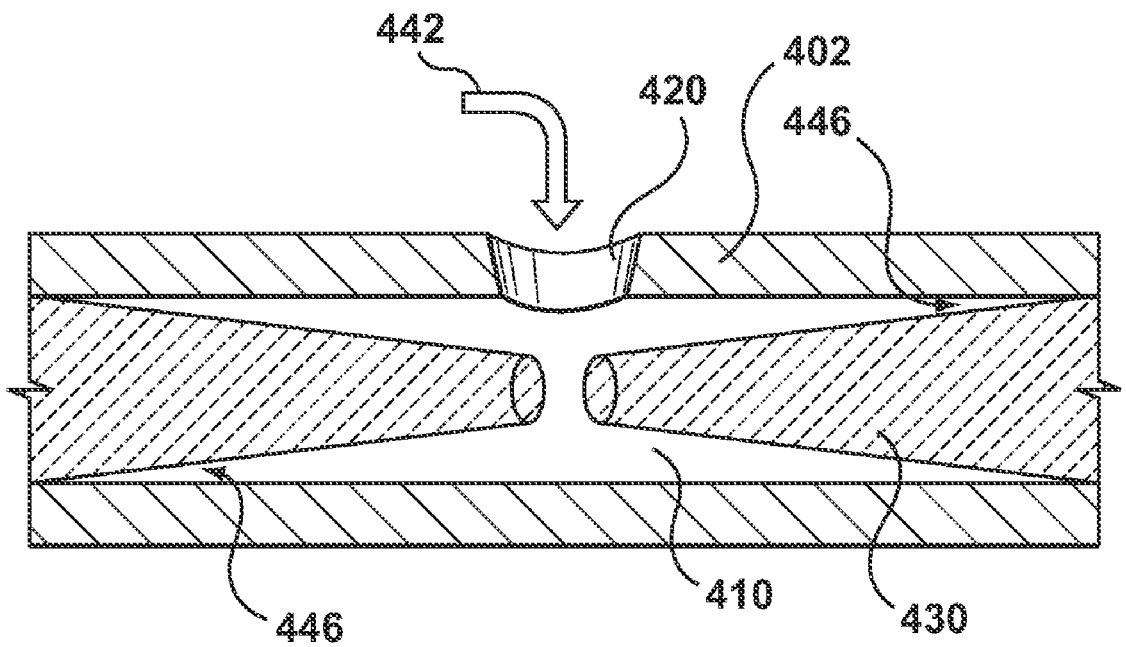

Step 470 can be accomplished in any manner known to those of ordinary skill in the art. Further, step 470 can be performed as part of step 465, or thereafter. In one particular non-limiting example, hydrofluoric and nitric acid are used as an etchant 442 with an outer member 402 made from MP35N and a core member 403 made from tantalum. In such an example, the etchant 442 preferentially etches the core member 430 from the interface 446 of the core member 430 and outer member 402, as shown in FIG. 25. When performing such a step after the core member has been removed from the struts 406, the etchant 442 begins to remove core member 430 from the core member 430 outer member 402 interface at the crowns 408, as shown in FIG. 28. Continuing this process results in lumens 448 created between the outer walls of core member 430 remaining in the crowns 408 and the inner wall of outer member 402, as shown in FIG. 28. Those of ordinary skill in the art would recognize that the etchant used for step 470 may also be used for step 465 such that both steps are performed simultaneously. Further, those of ordinary skill in the art would recognize that other etchant/core member/outer member combinations may be used provided that they permit a lumen through or around the core member without removing the entire core member.

After core member 430 has been removed from the strut regions and a lumen 448 has been provided through crowns 408, a biologically or pharmacologically active substance 416 may be injected into lumens 410/448, as shown in step 475 of FIG. 23. This produces a hollow wire or outer member 402 with biologically or pharmacologically active substance 416 disposed in lumens 410, 448 at struts 406 and crowns 408, respectively, and openings 420 through which biologically or pharmacologically active substance 416 may be eluted, as shown FIGS. 22 and 28. Lumen 410 may be filled with biologically or pharmacologically active substance 416 by the methods described in co-pending U.S. application Ser. Nos. 12/884,503; 12/884,578; 12/884,362; 12/884,451; 12/884,596; and Ser. No. 12/884,501 all of which were filed on Sep. 17, 2010, each of which is incorporated by reference herein in its entirety, or any other suitable method known to those skilled in the art.

Further processing of the stents in the above-described embodiments, such as annealing, cleaning, and other processes known to those skilled in the art, can be performed at appropriate times in the methods described above. For example, and not by way of limitation, annealing the stent may take place before filling the stent with the biologically or pharmacologically active substance if the annealing step may damage the substances. Similarly, a final cleaning step may occur after filling the stent with the biologically or pharmacologically active substance. Further, openings used to allow an etchant access to the lumen to remove the core member or used to fill the lumen with a biologically or pharmacologically active substance may be closed control the elution rate and elution time of the biologically or pharmacologically active substance from the stent.

The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus (rapamycin) or other limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

The stents described herein may be used conventionally in blood vessels of the body to support such a vessel after an angioplasty procedure. It is known that certain biologically or pharmacologically active substances eluted from stents may prevent restenosis or other complications associated with angioplasty or stents. The stents described herein may alternatively be used in other organs or tissues of the body for delivery of drugs to treat tumors, inflammation, nervous conditions, or other conditions that would be apparent to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a stent comprising the steps of:
    utilizing an elongated composite member including an outer member and a core member disposed within a lumen of the outer member;
    shaping the composite member into a stent pattern including a waveform having a plurality of struts interconnected by crowns;
    forming openings through the outer member;
    after the step of shaping the composite member into the pattern, processing the composite member such that the core member is removed from at least a plurality of the struts of the waveform without adversely affecting the outer member and such that the core member is not removed from at least a plurality of the crowns of waveform, thereby leaving the outer member with a lumen in at least a plurality of the struts and the outer member with the core member in at least a plurality of the crowns.

2. The method of claim 1, further comprising the step of filling the lumens with a biologically or pharmacologically active substance after the core member has been removed.

3. The method of claim 2, wherein the biologically or pharmacologically active substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

4. The method of claim 1, wherein the step of processing the composite member comprises exposing the composite member to an etchant that reacts with the core member to remove the core member, wherein the etchant does not react with the outer member.

5. The method of claim 4, wherein the etchant is a liquid chemical that dissolves the core member.

6. The method of claim 5, wherein the etchant is a gas.

7. The method of claim 6, wherein the outer member is formed from MP35N, the core member is formed from one of tantalum, tungsten, molybdenum, niobium, rhenium, carbon, germanium, and silicon, and the etchant is xenon difluoride.

8. The method of claim 4, wherein the core member is soluble in the etchant and the outer member is not soluble in the etchant.

9. The method of claim 1, wherein the core member is removed from all of the struts.

10. The method of claim 1, wherein the core member is not removed from any of the crowns.

11. The method of claim 1, wherein the core member is more radiopaque than the outer member.

12. The method of claim 1, further comprising the step of removing a portion of the core member in the at least a plurality of crowns with the core member remaining such that a lumen is provided through the crowns while a portion of the core member remains in the crowns.

13. A method of forming a stent comprising the steps of:
    utilizing a plurality of elongated composite members, each composite member including an outer member and an inner member disposed within a lumen of the outer member;
    shaping each composite member into a waveform having a plurality of struts interconnected by crowns;
    wrapping each waveform into a cylindrical element;

aligning the cylindrical elements along a common longitudinal axis and joining the cylindrical elements together to form a tubular stent;

forming openings through the outer members;

after the step of shaping the composite members into a waveform, processing the composite members such that the inner member is removed from at least a plurality of the struts of the waveform without adversely affecting the outer member and such that the core member is not removed from at least a plurality of the crowns of the waveform, thereby leaving the outer member with a lumen in at least a plurality of the struts and the outer member with a core member in at least a plurality of the crowns.

14. The method of claim 13, further comprising the step of filling the lumens with a biologically or pharmacologically active substance after the core member has been removed.

15. The method of claim 14, wherein the biologically or pharmacologically active substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

16. The method of claim 13, wherein the step of processing the composite member comprises exposing the composite member to an etchant that reacts with the core member to remove the core member, wherein the etchant does not react with the outer member.

17. The method of claim 16, wherein the etchant is a liquid chemical that dissolves the core member.

18. The method of claim 17, wherein the etchant is a gas.

19. The method of claim 18, wherein the outer member is formed from MP35N, the core member is formed from one of tantalum, tungsten, molybdenum, niobium, rhenium, carbon, germanium, and silicon, and the etchant is xenon difluoride.

20. The method of claim 16, wherein the core member is soluble in the etchant and the outer member is not soluble in the etchant.

21. The method of claim 13, wherein the core member is removed from all of the struts.

22. The method of claim 13, wherein the core member is not removed from any of the crowns.

23. The method of claim 13, wherein the core member is more radiopaque than the outer member.

24. The method of claim 13, further comprising the step of removing a portion of the core member in the at least a plurality of crowns with the core member remaining such that a lumen is provided through the crowns while a portion of the core member remains in the crowns.

* * * * *